United States Patent [19]
Burch et al.

[11] Patent Number: 6,130,250
[45] Date of Patent: Oct. 10, 2000

[54] VETERINARY USE OF A PLEUROMUTILIN DERIVATIVE

[75] Inventors: David George Sidney Burch, Berkshire; Paul Howard Ripley, Tonbridge, both of United Kingdom; Erich Zeisl, Jenbach, Austria

[73] Assignee: Biochemie Gesellschaft m.b.H., Kundl, Austria

[21] Appl. No.: 09/214,164

[22] PCT Filed: Jul. 3, 1997

[86] PCT No.: PCT/EP97/03518

§ 371 Date: Jul. 2, 1999

§ 102(e) Date: Jul. 2, 1999

[87] PCT Pub. No.: WO98/01127

PCT Pub. Date: Jan. 15, 1998

[30] Foreign Application Priority Data

| Jul. 4, 1996 | [GB] | United Kingdom | 9614012 |
| Jul. 4, 1996 | [GB] | United Kingdom | 9614013 |
| Jul. 4, 1996 | [GB] | United Kingdom | 9614014 |
| Jul. 4, 1996 | [GB] | United Kingdom | 9614015 |
| Jul. 4, 1996 | [GB] | United Kingdom | 9614016 |
| Jul. 4, 1996 | [GB] | United Kingdom | 9614017 |
| Jul. 4, 1996 | [GB] | United Kingdom | 9614018 |
| Jul. 4, 1996 | [GB] | United Kingdom | 9614019 |

[51] Int. Cl.$^7$ ........................................................ A61K 31/22
[52] U.S. Cl. ........................................................... 514/550
[58] Field of Search .............................................. 514/550

[56] References Cited

U.S. PATENT DOCUMENTS 4,675,330  6/1987  Berner .
5,164,526  11/1992  Macher .

FOREIGN PATENT DOCUMENTS 392272A  2/1991  Austria .
3405632A  8/1985  Germany .

OTHER PUBLICATIONS

Horkovics–Kovats et al., "Physiologically based pharmacokinetic modelling with valnemulin and its metabolites after multiple oral administration in pigs", J. Pharm. Med., vol. 6, No. 3–4, 1996, pp. 149–167.

*Primary Examiner*—Gary Geist
*Assistant Examiner*—Leigh C. Maier
*Attorney, Agent, or Firm*—Michael P. Morris; Lydia T. McNally; Stephen G. Kalinchak

[57] ABSTRACT

Use of the compound of formula I (as described in the specification) in the therapy of veterinary diseases, the expression of which is enhanced by increasing stock density.

10 Claims, No Drawings

VETERINARY USE OF A PLEUROMUTILIN DERIVATIVE

This application is a 371 of PCT/EP97/03518 filed Jul. 3, 1997.

The invention relates to pleuromutilin derivatives. It concerns the veterinary use of the compound of formula I

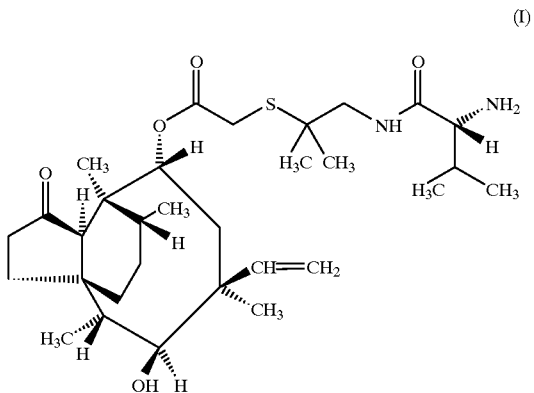

i.e. 14-O-[1-[(R)-2-amino-3-methylbutyrylamino]-2-methylpropan-2-ylthioacetyl]mutilin in free base or in veterinarily acceptable salt form, in the therapy of veterinary diseases the expression of which is enhanced by increasing stocking density, hereinafter briefly named "the use of the invention."

The compound of formula I in free base or in veterinarily acceptable salt form (Econor®) is hereinafter briefly named "the agent of the invention". It preferably is in salt, especially in hydrochloride salt form. In that form it is known under the generic name valnemulin hydrochloride.

The term "therapy" is to be understood as applying for prophylactic as well as curative treatment.

The compound of formula I in free base form or in chemotherapeutically or veterinarily acceptable salt form is known from e.g. EP 153 277 and its equivalents, e.g. U.S. Pat. No. 4,675,330, specifically as Example 12 therein.

Known therefrom is, further, an inhibitory activity against various bacteria in vitro, at concentrations of ca. 0.008 to 25 μg/ml;

an inhibitory activity in vitro against mycoplasms and chlamydia generally, at concentrations of ca. 0.008 to 0.5 μg/ml;

an inhibitory activity in vivo in mice, using various bacterial strains, and on hens, using mycoplasm strains, at a dosage of ca. 12 to 50 mg/kg body weight;

an anti-parasitic activity, in particular in vivo against coccidia in fowl, at dosages of 20–150 mg/kg of feed; and growth-promoting activity in hen and pig in vivo, at a dosage of 10–50 mg/kg of feed, thus making the compound useful as an antibacterially active antibiotic generally and, as a veterinary agent, in particular for the chemotherapeutic treatment of coccidioses in fowl as well as a growth promoter in hen and pig.

It has now been found that, surprisingly, the agent of the invention is particularly effective in the therapy of veterinary diseases the expression of which is enhanced by increased stocking density, such as enzootic pneumonia in swine caused by *Mycoplasma hyopneumoniae* infection, swine dysentery caused by *Serpulina* (formerly Treponema) *hyodysenteriae* infection, swine colitis (inflammation of the colon) associated with *Serpulina pilosicoli* infection, ileitis in swine (porcine proliferative enteropathy; porcine intestinal adenomatosis) associated with *Lawsonia intracellularis* infection, chronic respiratory disease and arthritis in poultry associated with *Mycoplasma gallisepticum* infection, secondary pneumonia in swine associated with *Pasteurella multocida, Actinobacillus* (Haemophilus) *pleuropneumoniae* and/or *Haemophilus parasuis* infection, pneumonia in lambs, sheep and cattle (Shipping Fever, Transit Fever, Calf Respiratory Complex, Bovine Pneumonic Pasteurellosis) associated with *Pasteurella haemolytica* infection and polyarthritis in swine associated with *Mycoplasma hyosynoviae* infection.

Further, even more surprisingly, it has been found that induction of resistance to the drug is extremely low.

The invention thus concerns the veterinary use as defined above.

It also concerns the use of the agent of the invention for the manufacture of a medicament for use in the therapy of veterinary diseases the expression of which is enhanced by increasing stocking density.

It further concerns a method of treatment of veterinary diseases the expression of which is enhanced by increasing stocking density, comprising administration of a therapeutically effective amount of the agent of the invention to an animal in need of such treatment.

It further concerns a veterinary agent for use in the therapy of veterinary diseases the expression of which is enhanced by increasing stocking density, comprising the compound of formula I in free base or in veterinarily acceptable salt form, together with at least one veterinarily acceptable carrier or diluent.

If further concerns a process for the preparation of a medicament for use as defined above, which comprises mixing the agent of the invention together with at least one veterinarily acceptable carrier or diluent.

The animal suffering from veterinary diseases the expression of which is enhanced by increasing stocking density may e.g. not already be treated antibacterially with the agent of the invention, or not already be receiving the agent of the invention for growth promotion.

A) *Mycoplasma hyopneumoniae* infection:

*Mycoplasma hyopneumoniae* infection may be diagnosed in conventional manner, e.g. as described in veterinary manuals such as Taylor, D. J., in *Pig Diseases,* 6th Ed. (1995), Publ. D. J. Taylor, Glasgow, U.K. on page 164–165. The beneficial activity of the agent of the invention in this use is determined e.g. as follows:

1. Activity in vitro:

Ten field isolates from outbreaks of enzootic pneumonia in different herds and the type strain "J" are included in the test. The isolates are filter-cloned, identified by the disc growth inhibition test and used in 7th to 10th passage. The test for minimal inhibitory concentration (MIC) is performed in liquid medium (Friis, N. F. et al., *Acta Vet. Scand.* 32 [1991] 425–429) in tubes of 1.8 ml containing 2-fold concentration of valnemulin and tiamulin hydrogen fumarate. The mycoplasmas are inoculated in 10 fold dilutions, and the cultures read visually for growth using tubes seeded with $10^2$ to $10^4$ colour forming units. Initial reading is performed after 2–4 days and final reading after 10–14 days, when no further progression in colour shift has taken place. MIC is determined as the lowest concentration of test compound showing inhibition of growth compared to control (Friis, N. F. and Szancer, J., *Acta Vet. Scand.* 35 [1994] 389–394).

The results are shown in Table 1:

TABLE 1

| | MIC (μg/ml) | | | |
|---|---|---|---|---|
| | Valnemulin (ch) | | Tiamulin (hfu) | |
| Number of strains | Initial | Final | Initial | Final |
| 1 | 0.0010 | 0.0025 | 0.025 | 0.050 |
| 1 | 0.0010 | 0.0025 | 0.025 | 0.100 |
| 3 | 0.0010 | 0.0025 | 0.050 | 0.100 |
| 5* | 0.0025 | 0.0025 | 0.050 | 0.100 |
| 1 | 0.0025 | 0.0025 | 0.100 | 0.100 |

*comprises type strain ch = hydrochloride hfu = hydrogen fumarate

All *M. hyopneumoniae* strains tested are highly susceptible to the effect of valnemulin with MIC values 10–40 times less than those for tiamulin, both at the initial and final readings, making the compound particularly interesting for use in treatment of clinical cases in infected herds.

2. Activity in vitro:

Tissue samples are obtained from the lungs of pigs from various enzootic pneumonia of pigs (EPP)-affected herds. Samples are shipped on dry ice for culture. *M. hyopneumoniae* is recovered from freshly sectioned lung tissue by direct culture onto Mycoplasma Experience agar. This technique allows the distinctive colonies of *M. hyopneumoniae* to be recognised and readily separated, by cloning from other faster growing mycoplasma species such as *Mycoplasma hyorhinis*, often present in EPP lung samples. Isolates are subcultured and identified by disc growth inhibition using specific rabbit antiserum raised to *M. hyopneumoniae* NCTC 10110.

Cultures for antibiotic challenge are prepared in Mycoplasma Experience broth, incubated aerobically at 36° C.

A commercially available solid medium (Mycoplasma Experience Ltd.) is used to isolate *M. hyopneumoniae* from lung tissue. A liquid medium (Mycoplasma Experience Ltd.) containing phenol red and glucose (pH 7.6) is used for the MIC assays.

Stock solutions of test compound are prepared at 1 mg/ml concentration in deionised water, sterilised by filtration through 0.2μ pore size membrane filters (Sartorius Minisart, N) and stored at −20° C. For use in the MIC tests the stock solutions are diluted in liquid medium to double the final concentrations required. MIC tests are carried out according to the method of Tanner & Wu, *Avian Diseases* 36 (1992) 714–717. Actively growing challenge cultures are prepared either from 1 ml aliquots of broth cultures stored at −70° C. or from cultures stored on agar at −70° C. The challenge cultures are diluted to give a target titre of $10^3$ to $10^5$ colour changing units/ml. 0.1 ml aliquots of challenge inocula are mixed with 0.1 ml aliquots of antibiotic dilution in microtitre wells. Each microtitre plate contains uninoculated media at pH 6.8 (*M. hyopneumoniae*) (end point control) and antibiotic-free inoculated challenge controls. All plates are sealed with adhesive film and incubated aerobically at 36° C. MICs are recorded when the colour change in the challenge control wells match the pH of the end point control. The MIC is the lowest concentration showing no colour change.

The results are shown in Table 2 for valnemulin and the two reference compounds tiamulin and enrofloxacin:

TABLE 2

In vitro sensitivity of ten field isolates of *M. hyopneumoniae*

| | MICs (μg/ml) | | | Type Strain J |
|---|---|---|---|---|
| | Field Strains (n = 10) | | | |
| Antibiotic | 50% | 90% | Range | (NCTC 10110) |
| Valnemulin (ch) | 0.0005 | 0.001 | 0.00025–0.001 | 0.0025 |
| Tiamulin (hfu) | 0.025 | 0.05 | 0.01–0.05 | 0.1 |
| Enrofloxacin | 0.005 | 0.01 | 0.0025–0.025 | 0.025 |

All strains were found to be highly susceptible to valnemulin. Most of the strains showed a very good sensitivity to enrofloxacin but for individual strains the MIC of valnemulin was at least five times lower, even with those sensitive to 0.0025 μg/ml of enrofloxacin. These results confirm that field isolates are extremely sensitive to valnemulin.

3. Development of resistance:

*Mycoplasma hyopneumoniae* reference strain NCTC 10110 (obtained from the National Collection of Type Cultures, London, UK) and a recent field isolate (MEVT G23), are grown aerobically at 36° C. in *Mycoplasma glucose* broth containing phenol red until an acid colour change occurs. After addition of sterile glycerol (5% v/v) the cultures are dispensed in 1 ml aliquots and frozen at −70° C. These cultures are used to initiate further broth cultures which are titrated to obtain the number of colour changing units (ccu) in microtitre plates after incubation (36° C.). Replication allows challenge of antibiotic dilutions with predetermined numbers of ccu in minimal inhibitory concentration (MIC) tests and in the primary passage in habituation studies.

A commercially available medium (Mycoplasma Experience Ltd.) containing glucose and phenol red (MEGB) is used at pH 7.6.

Stock test compound solutions are prepared at 1000 μg/ml in deionized water. After vortexing, the solutions are sterilized by filtration through 0.2μ pore size membrane filters (Sartorius Minisart, N). For use in the MIC tests the stock solutions are diluted in mycoplasma broth to double the final concentrations required. In habituation studies the stock solutions are dispensed in 1 ml aliquots and frozen at −20° C. These are thawed and used at 5 day–7 day intervals to prepare ranges of concentrations of drug (doubling series) in MEGB, in 1.9 ml aliquots, covering the MICs against both strains of *M. hyopneumoniae*. Oxytetracycline hydrochloride is prepared fresh on each occasion. The dilution ranges are gradually changed from passage to passage to allow for the development of resistance in the mycoplasmas.

Test procedures:

MIC tests are carried out by the method of Tanner & Wu, *Avian Diseases* 36 (1992) 714–717 before carrying out the habituation study (below) and after the 10th passages 0.1 ml aliquots of the compound dilution are mixed with 0.1 ml aliquots of the challenge inocula, containing between $10^3$ and $10^5$ colour changing units (ccu) per ml, in microtitre wells. Each microtitre plate contains uninoculated medium, medium at pH 6.8 (end-point-control) and drug-free inoculated challenge controls. All plates are sealed and incubated aerobically at 36° C. MICs are recorded when the colour change in the challenge control wells match the pH 6.8 control (orange-yellow). The MIC is the lowest concentration to show no colour change.

Habituation study: In the primary passage experiment, 1.9 ml volumes of antibiotic solutions at concentrations covering the MIC of the *M. hyopneumoniae* strain under test, are inoculated with 0.1 ml of broth culture containing between $10^3$ ccu/ml to $10^5$ ccu/ml. A growth control consisting of drug-free broth inoculated with *M. hyopneumoniae* and an uninoculated medium control are included in each passage experiment. After 7 days incubation (36° C.) the two highest concentrations of drug-containing broth showing an acid colour change are pooled and used to inoculate a fresh series of drug dilutions in mycoplasma broth (0.1 ml culture into 1.9 ml drug-containing broth). This process is repeated every 5–7 days for up to 10 passages. When the mycoplasma strains become resistant to particular antibiotics, or at the 10th passage, each strain is grown once more in drug-containing broth and the MICs determined.

Results: The MICs of the *M. hyopneumoniae* strain "J" and a field isolate before and after exposure to the antibiotics are shown in Table 3:

TABLE 3

In vitro development of resistance in two strains of *M. hyopneumoniae*

| Compound | Strain | Pre-passage MIC (μg/ml) | Post-passage MIC up to P10/P11[1] (μg/ml) | Resistance increase (fold increased) |
|---|---|---|---|---|
| Valnemulin (ch) | NCTC 10110 | 0.0025 | 0.005 | 2 |
|  | Field isolate | 0.001 | 0.0025 | 2.5 |
| Tylosin tartrate | NCTC 10110 | 0.25 | >500[2] | >2000 |
|  | Field isolate | 0.125 | 62.5[2] | 500 |
| Oxytetracycline hydrochloride | NCTC 10110 | 0.25 | 1.0 | 4 |
|  | Field isolate | 0.25 | 1.0 | 4 |

[1] In vitro passage level
[2] MIC after 8 passages in mycoplasma broth containing tylosin It was found that before exposure both strains were highly susceptible to valnemulin, with MICs of 0.0025 μg/ml for the reference strain and 0.001 μg/ml for the field isolate. These levels of activity were 50–100 told greater than those of tylosin and oxytetracycline. These MIC results were used to select dilution ranges for the drugs in the habituation study.

After 10 cycles of exposure to valnemulin, resistance development was minimal in both strains of *M. hyopneumoniae*, the MICs increasing from 0.0025 μg/ml to 0.005 μg/ml and from 0.001 μg/ml to 0.0025 μg/ml for the reference strain and the field isolate, respectively. In contrast, marked resistance developed to tylosin tartrate in both strains of *M. hyopneumoniae*. In the reference strain resistance first occurred within 4 to 5 passages in tylosin-containing broth and by the eighth passage the MIC had risen to >500 μg/ml, reflecting a >2000 told increase in resistance to this antibiotic (Table 3). Marked tylosin resistance developed in the field isolate within 8 passages, the MIC rising 500-fold to 62.5 μg/ml. This level of resistance persisted after 10–11 passages in tylosin-containing broth. 4-fold increases in resistance to oxytetracycline occurred in both strains of *M. hyopneumoniae* during 10 cycles of exposure, the MICs rising from 0.25 μg/ml to 1 μg/ml.

These results show that valnemulin is considerably more active against *M. hyopneumoniae* than either tylosin or oxytetracycline and that it does not induce significant resistance to itself in *M. hyopneumoniae* strains.

4. Prevention of experimentally-induced enzootic Pneumonia in vivo:

An experimental model of enzootic pneumonia, using passaged lung material originally derived by infection of gnotobiotic pigs with *M. hyopneumoniae*, was employed to assess the potential of valnemulin for prevention of the disease. Three trials were performed: Trials 1 and 2 were dose titration studies of the novel compound using a standard challenge strain of *M. hyopneumoniae* and in Trial 3, the efficacy of the compound at 200 ppm in feed against a second challenge strain was assessed. Large white Landrace male pigs, 6–7 weeks of age, from stock free of infection with *M. hyopneumoniae* are used. The challenge materials are pneumonic lungs containing *M. hyopneumoniae* given as a homogenate intranasally on three successive days. The minimum inhibitory concentration (MIC) of valnemulin against the strain present in material used in Trials 1 & 2 was 0.016 μg/ml and that for the strain isolated from material used in Trial 3 was 0.0078 μg/ml. The challenge material was originally derived by infection of gnotobiotic pigs with *M. hyopneumoniae* and subsequent passage in SPF (Specific Pathogen-free) pigs and had been stored below −70° C.

Trial 1: Medication with valnemulin hydrochloride by stomach tube (gavage) once a day at 0 (control), 2.5, 5, 7.5 or 10 mg/kg body weight per day. Six pigs per group.

Trial 2: Medication with valnemulin hydrochloride in feed at 0, 100, 200, 300 or 400 ppm (equivalent to 0, 5, 10, 15 and 20 mg/kg/day). Six pigs per group.

Trial 3: Medication with valnemulin hydrochloride in feed at 0 or 200 ppm (equivalent to 0 and 10 mg/kg/day). Eight pigs per group. Medication was given from the first day of challenge infection until post-mortem examination performed approximately 3 weeks after challenge infection. Disease was assessed by quantifying lung lesions [Cambridge lung lesion scoring system (Goodwin, R. F. W. and Whittlestone, P., *J. Hyg.* 69 [1971] 391–397), in which the score is an approximation of percent of lung affected with pneumonia], by estimation of lung-bodyweight ratio and by isolation of *M. hyopneumoniae* from lungs.

The results are shown in Table 4:

TABLE 4

| Medication | Lung lesion score | Lung-bodyweight ratio (%) |
|---|---|---|
| Trial 1: Medication by gavage, MIC 0.016 μg/ml[1] | | |
| 0 | 13.2 | 1.35 |
| 10 mg/kg/day | 1.7 | 1.08 |
| 7.5 mg/kg/day | 3.8 | 1.21 |
| 5 mg/kg/day | 11.1 | 1.31 |
| 2.5 mg/kg/day | 7.7 | 1.21 |
| Trial 2: Medication by feed, MIC 0.016 μg/ml | | |
| 0 | 22.1 | 1.61 |
| 400 ppm (20 mg/kg)[2] | 6.3 | 1.24 |
| 300 ppm (15 mg/kg) | 12.7 | 1.27 |
| 200 ppm (10 mg/kg) | 12 | 1.29 |
| 100 ppm (5 mg/kg) | 25 | 1.53 |
| Trial 3: Medication by feed, MIC 0.0078 μg/ml | | |
| 0 | 10.8 | 1.32 |
| 200 ppm (10 mg/kg) | 2.3 | 1.21 |

[1] MIC of valnemulin hydrochloride in μg/ml against *M. hyopneumoniae* isolated from challenge material
[2] Approximate daily dose of valnemulin hydrochloride per pig In Trial 1, unmedicated, challenged pigs had a mean lesion score of 13.2. Valnemulin reduced lesions by 71% and 87% at doses of 7.5 and 10 mg/kg, respectively, while at 2.5 and 5 mg/kg/day it was somewhat less effective at reducing lesions. *M. hyopneumoniae* was reisolated from fewer pigs medicated with 10 mg/kg, in comparison with pigs medicated with 2.5 mg/kg (1 vs. 4 pigs).

In Trial 2, unmedicated challenged pigs had a mean lesion score of 22.1. Pigs medicated with valnemuiin at 200, 300 or 400 ppm showed reductions in lesions of 46%, 43% and 71%, respectively. Lung weights, which might reflect microscopic lesions as well as gross lesions, showed a more dramatic effect, with significant reductions at levels down to 200 ppm. No reduction in lesions was seen in pigs medicated at 100 ppm. *M. hyopneumoniae* was reisolated from all unmedicated pigs at post-mortem examination, but was not reisolated from pigs medicated with 400 ppm or 300 ppm of valnemulin. It was reisolated from 3 and 4 pigs medicated with 200 ppm and 100 ppm, respectively.

In Trial 3, unmedicated pigs had a mean lesion score of 10.8; medication with valnemulin at 200 ppm in feed reduced the lesion scores by 79%. There was no difference in the levels of *M. hyopneumoniae* detected at post-mortem examination between medicated and unmedicated pigs.

Valnemulin thus proves effective for the prevention of experimentally-induced enzootic pneumonia of pigs in separate experiments using challenge material containing two different strains of *M. hyopneumoniae*.

The agent of the invention is therefore useful in the therapy of enzootic pneumonia in swine caused by *Mycoplasma hyopneumoniae* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at a daily dosage of from about 5 mg/kg to about 15 mg/kg animal body weight, suitably given in divided doses two to four times daily, or in sustained release form. For most animals the total daily dosage is from about 100 mg to about 1000 mg, preferably from about 100 mg to about 500 mg, given once or twice daily.

It may advantageously be administered as sole therapy.

Preferred doses in drinking water are from 0.01 to 0.05% weight by volume, particularly 0.01 to 0.025%, and in feed from 100 to 400 ppm (g/metric tonne), particularly 100 to 200 ppm (g/metric tonne).

B) *Serpulina hyodysenteriae* infection:

*Serpulina hyodysenteriae* infection may be diagnosed in conventional manner, e.g. as described in veterinary manuals, such as Taylor, D. J., in *Pig Diseases*, 6th Ed. (1995), Publ. D. J. Taylor, Glasgow, U.K. on page 143–144. The beneficial activity of the agent of the invention in this use is determined e.g. as follows:

1. MIC determination;

Nine field isolates of *S. hyodysenteriae* from outbreaks of swine dysentery and the type strain, ATCC 31212 are included, and ATCC 29796 (*Serpulina innocens*, group 3 (Fellström, C., *Res. Vet. Sci.* 59 [1995] 1–4). Identification is based on pattern of hemolysis on TSA (Tryticase soy agar) with 5% bovine blood, and on test for indole production and hippurate hydrolysis (Rosco Diagnostic Tablets, Taastrup, DK). The bacteria are transferred from agar plates into 0.9% saline and turbidity adjusted to 1.0 on the McFarland scale before 10 μl of each isolate is inoculated on agar plates with two-fold concentrations of valnemulin hydrochloride, tiamulin hydrogen fumarate, dimetridazole, lincomycin hydrochloride, and tylosin. Growth and hemolysis are recorded after 4 days of growth anaerobically and MIC is determined as the lowest concentration of antibiotics where the spirochetes do not grow.

The results of the MIC determinations for *S. hyodysenteriae* are shown in Table 5:

TABLE 5

Minimal inhibitory concentration (MIC) values for 10 *Serpulina hyodysenteriae* strains

| MIC (μg/ml) | Antimicrobial | | | | |
|---|---|---|---|---|---|
| | Valnemulin (ch) | Tiamulin (hfu) | Dimetri-dazole | Lincomycin | Tylosin |
| 0.0156 | 2 | — | | | |
| 0.0312 | 4 | — | | | |
| 0.0625 | 3 | — | — | | |
| 0.125 | | 6 | — | | |
| 0.250 | | 1 | — | | |
| 0.500 | | 1 | 2 | — | |
| 1 | 1 | 2 | 2 | — | |
| 2 | | | 1 | | — |
| 4 | | | | | |
| 8 | | | 1 | | — |
| 16 | | | 1 | | |
| 32 | | | | — | |
| 64 | | | 3 | 1 | |
| 128 | | | | 3 | 1 |
| >128 | | | | 6 | 9 | ch = hydrochloride  hfu = hydrogen fumarate

All the *S. hyodysenteriae* strains were highly susceptible for valnemulin, showing MIC values 2–32 times less than those of tiamulin. The high suceptibility of vainemulin for *S. hyodysenteriae* makes the compound interesting for use in treatment of clinical cases in infected herds.

2. MIC determination:

Minimum inhibitory concentrations (MICs) are determined against 10 strains of *S. hyodysenteriae* isolated from porcine faeces, by the agar dilution method. NCTC (National Collection of Type Cultures) strains or reference strains are used as controls in all MIC tests. The agar medium for *S. hyodysenteriae* consists of BAB2 (Unipath CM271) containing 7% whole defibrinated sterile sheep blood. All antimicrobial agents are tested in doubling dilutions. Prepared antibiotic dilutions are added to an appropriate volume of MH agar, previously cooled to 50° C., mixed and 20 ml volumes poured. All *S. hyodysenteriae* incubations are performed in an anaerobic work station at 37° C. (+/−0.5° C.) (Don Whitley Scientific) which provides a strict anaerobic atmosphere comprising 80% nitrogen, 10% hydrogen and 10% carbon dioxide. All other incubations are performed at 37° C. All strains are incubated in an aerobic atmosphere at 37° C. for 24 hours. The numbers of the organisms are adjusted to an optical density (OD) equivalent to $1 \times 10^8$ colony forming units (cfu) per ml, using MH broth as a blank. The antibiotic containing plates are inoculated in duplicate using a multipoint inoculator (Denley Instruments) which delivers a plate inoculum of approximately 1 μl giving an inoculum of $10^4$–$10^5$ cfu per spot for all strains (Amon, *J. Antimicrob. Chemother.* 21 [1988] 701–710; Ericsson et al., *Acta Pathol. Microbiol. et Immunol. Scand.* 217 [1971] (B) Suppl., 1–90). Control plates are incubated under the same conditions as the test plates. The MICs are read after 24 and 48 hours, the latter being the definitive reading. The MIC is defined as the lowest concentration of antibiotic on which there is no growth, disregarding a single colony or a faint haze caused by the inoculum (National Committee for Clinical Laboratory Standards [1989], *Antimicrobial Susceptibility Testing*, NCCLC Publications SC3, Villanova, Pa., USA).

The MIC (in μg/ml) against *Serpulina hyodysenteriae* were valnemulin (0.1), tiamulin (0.3), lincomycin (50.0), tylosin (200.0) and dimetridazole (30.0). All strains of *S. hyodysenteriae* were susceptible to valnemulin, which was the most active of the agents tested by 3–600 fold.

3. Challenge trial:

Two trials were effected where valnemulin fed at various inclusion levels is compared to tiamulin for the prevention of swine dysentery. The severity of disease is assessed by the evidence of clinical disease as determined by clinical scores for body condition, faeces consistency and composition. The excretion of *Serpulina hyodysenteriae* in faeces, lesions at post-mortem examination, growth rate and feed conversion ratio are also determined.

In the first trial valnemulin hydrochloride fed at 20, 30 and 40 ppm is compared with tiamulin hydrogen fumarate fed at 30 ppm and with unmedicated controls. Five groups of 9 (5 to 6 week old) conventionally reared pigs are used for each treatment group. The pigs are fed unmedicated food for 14 days, then challenged with the standard strain of *S. hyodysenteriae* (P18A). Challenge is by the oral route on two consecutive days. The medicated feed is introduced on the day after the second challenge. In the second trial a similar procedure is followed except that 4 groups of approximately 9 pigs were used. These are fed valnemulin hydrochloride at 5, 10 and 20 ppm and compared to unmedicated controls. In this trial the pigs used are from an outdoor reared herd and are challenged with a strain of *S. hyodysenteriae* isolated from an outdoor herd and previously shown to be capable of causing swine dysentery. In both trials the evidence of clinical disease is assessed daily and a clinical score assigned, rectal swabs are taken twice weekly for isolation of *S. hyodysenteriae* and all pigs are weighed at regular intervals. Food intake is also recorded. A post-mortem examination is carried out 21 days after challenge and the large intestine examined for the presence of lesions. Mucosal scrapings are also taken from 4 areas in the large intestine and cultured for *S. hyodysenteriae*.

In the first trial, clinical swine dysentery was first seen in the unmedicated control group 8 days after challenge and 8 out of 9 pigs became affected. Clinical disease was also seen in 1 pig in the group fed valnemulin at 30 ppm and in 2 out of 9 animals in the tiamulin group. Evidence of disease was not seen in the 20 and 40 ppm valnemulin treated groups. A mean clinical score per pig of 36 was recorded for the control group compared to a score of 6 for the tiamulin treated group. The differences between the scores recorded for all the treatments groups were statistically different from the controls ($p<0.001$). *S. hyodysenteriae* was isolated from rectal swabs taken from all pigs in the control group and also from the 2 affected pigs in the tiamulin treated group. *S. hyodysenteriae* was also isolated from 2 pigs that received valnemulin fed at 30 ppm, this coincided with the clinical signs of swine dysentery seen subsequent to an incidental infection in this group. *S. hyodysenteriae* was not isolated from the 20 and 40 ppm groups. There was little difference in the weight gain or feed conversion ratio of all groups fed medicated food. At post-mortem examination the pigs in the control and tiamulin treated group that had clinical signs of disease showed typical lesions of swine dysentery consisting of adherent mucus with necrosis of the large intestine mucosal surface. Lesions were also seen in one pig in the tiamulin treated group and a control pig, both of which had not previously shown clinical signs of swine dysentery. *S. hyodysenteriae* was isolated from mucosal scrapings taken from all of these affected animals. One pig in the group fed vainemulin at 30 ppm also had lesions of swine dysentery but *S. hyodysenteriae* was not isolated from mucosal scrapings. Lesions were not seen at post-mortem examination in groups fed valnemulin at 20 and 40 ppm.

In the second trial clinical swine dysentery was first seen in the unmedicated control pigs 5 days after challenge and subsequently all 9 pigs in the group were affected and 6 of these had to be killed due to the severity of disease. In the group fed valnemulin at 5 ppm clinical signs of swine dysentery were first seen 8 days after challenge and subsequently 5 out of 10 animals were affected. However, the numbers affected in the valnemulin 5 ppm group were significantly less than the controls ($p<0.05$). Clinical signs of disease were not seen in groups fed valnemulin at 10 or 20 ppm. The mean clinical score of 11 for the valnemulin 5 ppm group was significantly less than the score of 77 for the controls ($p<0.005$). *S. hyodysenteriae* was isolated from rectal swabs taken from all control pigs during the trial. However, of the 5 animals affected in the valnemulin 5 ppm group *S. hyodysenteriae* was only isolated from 2 of these pigs. The pigs fed valnemulin at all levels were significantly heavier than the controls at the end of the trial (5 ppm, $p=0.05$; 10 and 20 ppm, $p<0.05$, respectively). At post-mortem examination typical lesions of swine dysentery were seen in the large intestinal mucosa of the 3 remaining control pigs. In the group fed valnemulin at 5 ppm, of the 5 pigs that originally had shown signs of disease only 2 of these had lesions at post-mortem examination but *S. hyodysenteriae* was not isolated from these animals. However, *S. hyodysenteriae* was isolated from mucosal scrapings taken from 2 other animals that had typical lesions at this time but had not shown clinical signs of disease. Lesions were not seen in the pigs fed valnemulin at either 10 or 20 ppm and *S. hyodysenteriae* was not isolated from these groups.

Thus valnemulin at inclusion rates down to 10 ppm is effective in preventing the occurrence of clinical signs of swine dysentery, the shredding of spirochaetes in faeces and the presence of lesions at post-mortum examination. At 30 ppm a few pigs did show clinical signs of swine dysentery but this coincided with an incidental infection which may have affected the intake of antibiotic. The effects of concurrent disease on the intake of antibiotic and the incidence of swine dysentery have previously been described (Burch, D. G. S., *Vet. Rec.* 110 [1982] 244–246). Analysis of weight gain data showed no differences between the treated groups indicating that the antibiotic did not effect palatability of the feed. At 5 ppm valnemulin did not completely prevent clinical disease or the shedding of spirochaetes but there were significant reductions in clinical scores and the shedding of spirochaetes when compared to the controls. In this trial tiamulin fed at 30 ppm did not prevent swine dysentery but reduced the incidence of disease when compared to the control group with a reduction in clinical scores. However, in this trial in-feed medication with valnemulin at 10 ppm is clearly more effective than Tiamulin at 30 ppm in preventing swine dysentery.

4. Further challenge trial:

A group of 60 (3.5 to 4 weeks old) conventionally reared pigs are fed unmedicated food for 14 days then challenged by the oral route with the standard strain of *S. hyodysenteriae* (P18A). When clinical signs of disease are evident, pigs are allocated to six treatment groups of 8 pigs per group and fed antibiotic containing feed for 10 days, then unmedicated food for a further 14 days. Valnemulin hydrochloride is fed at 50, 75, 100 and 150 ppm and compared with tiamulin hydrogen fumarate fed at 100 ppm and with unmedicated controls. Pigs with a range of clinical signs of disease are included in each treatment group. After allocation to the treatment groups the evidence of clinical disease is assessed daily and a clinical score assigned, rectal swabs are taken twice weekly for isolation of *S. hyodysenteriae* and all pigs are weighed at regular intervals. Food intake is also recorded. A post-mortem examination is carried out 24 days after challenge and the large intestine of each pig examined for the presence of lesions. Mucosal scrapings are also taken from 4 areas in the large intestine and cultured for *S. hyodysenteriae*.

After challenge and prior to allocation, clinical swine dysentery was seen 7 days after infection and the first 2 treatment groups (control and tiamulin) were formed 8 days after challenge. The other groups were formed 12, 15, 20 and 28 days after challenge in the following order: valnemulin at 75, 50, 100 and 150 ppm. Each group contained pigs that had blood and/or mucus in their faeces as well as animals that only had mild clinical signs for disease, i.e. soft faeces. On day 4 of the trial all pigs in the unmedicated control group were showing severe clinical signs of disease and were killed. During the treatment period, in the tiamulin group a total of 3 animals either died or required euthanasia due to severe swine dysentery. All pigs treated with valnemulin survived to the end of the trial. In the groups fed valnemulin at all levels the clinical signs of disease rapidly resolved and clinical disease was not seen by day 5 of the trial. By day 8 this improvement was also seen in the surviving pigs fed tiamulin. The mean clinical scores for the valnemulin groups ranged from 4 to 10 compared to a mean score of 30 recorded for the tiamulin group. Statistical analysis of clinical scores for days 3 to 10 showed that there was a significant difference between all groups fed valnemulin and the tiamulin treated group (p<0.001). All pigs fed valnemulin continued to increase in weight during the treatment period and all had a greater daily live weight gain (DLWG) than the tiamulin group (range 0.4 to 0.9 compared to 0.1). The feed conversion ratios (FCR) was much greater in the tiamulin treated group (6.4) compared to the valnemulin groups (range 1.9 to 2.5) during the treatment period. *S. hyodysenteriae* was isolated from the majority of pigs in each treatment group at the time of allocation. 5 days after allocation *S. hyodysenteriae* could not be detected in rectal swabs taken from pigs in any of the treatment groups.

In the post treatment period one pig in the group fed valnemulin at 50 ppm showed clinical signs of disease 4 days after the withdrawal of the medicated feed and one pig in the tiamulin treated group also had swine dysentery on the last day of the trial. However *S. hyodysenteriae* was not isolated from the faeces of these pigs. In this post-treatment period there was little observable difference in the DLWG or FCR between all of the treatment groups. At post-mortem examination at the end of the trial lesions of swine dysentery were not seen in any pig fed valnemulin at 75, 100 or 150 ppm. In the group fed valnemulin at 50 ppm, 1 pig had clinical swine dysentery and one other pig in this group had some reddening of the large intestine at this time. *S. hyodysenteriae* was also isolated from mucosal scrapings from these 2 pigs and from 3 other animals in this group that did not have lesions of swine dysentery. One pig in the group fed valnemulin at 75 ppm also yielded *S. hyodysenteriae* from mucosal scrapings although no evidence of clinical swine dysentery was seen in this pig.

Valnemulin at 50, 75, 100 and 150 ppm thus produced a reduction in the number of days that were needed to recover from clinical swine dysentery when compared to tiamuiin. Also animals did not die or require euthanasia in these valnemulin treated groups. There was a significant difference (p<0.001) in the clinical scores for the valnemulin treated groups compared to the tiamulin group. The shedding of *S. hyodysenteriae* in faeces was also prevented by all levels of valnemulin after the withdrawal of medicated feed. However, *S. hyodysenteriae* was isolated from mucosal scrapings from pigs receiving vainemulin at 50 and 75 ppm.

Tiamulin at 35 and 40 ppm has been shown to eliminate *S. hyodysenteriae* from faeces but not prevent the recovery from mucosal scrapings (Taylor, D. J., *Vet. Rec.* 106 [1980] 526–528). Tiamulin at 100 ppm has been successfully used under experimental conditions (Taylor, D. J., *Proc. 7th IPVS Congress Mexico* [1982] 47) to treat swine dysentery in animals that were not so severely affected that they were inappetent. In this trial tiamulin at 100 ppm reduced mortality compared to unmedicated controls but did not prevent some deaths, this may have been due to the severity of the disease induced by this experimental challenge.

In this trial valnemulin in feed at 50, 75, 100 and 150 ppm thus successfully treated experimentally produced swine dysentery with the prevention of mortality and elimination of clinical signs. *S. hyodysenteriae* excretion was prevented during treatment, with a relapse after treatment had ceased in just one animal treated with 50 ppm. Valnemulin at 50 and 75 ppm did not completely eliminate *S. hyodysenteriae* from all pigs but at 100 ppm was highly effective.

The agent of the invention is therefore useful in the therapy of swine dysentery caused by *Serpulina hyodysenteriae* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at a daily dosage of from about 1 mg/kg to about 5 mg/kg animal body weight, suitably given in divided doses two to four times daily, or ad libitum in feed or water, or in sustained release form. For most animals the total daily dosage is from about 10 mg to about 400 mg, e.g. from about 10 mg to about 200 mg for prevention or about 20 mg to about 400 mg for treatment, given ad libitum in feed or water, or once or twice daily.

Preferred doses in drinking water are from 0.001 to 0.05% weight by volume, particularly 0.001 to 0.005%, and in feed from 20 to 100 g/metric tonne, particularly 20 to 75 g/metric tonne.

C) Swine colitis associated with *Serpulina pilosicoli* infection:

Colitis may be diagnosed in conventional manner, e.g. as described in veterinary manuals such as Taylor, D. J., in *Pig Diseases*, 6th Ed. (1995), Publ. D. J. Taylor, Glasgow, U.K. on pages 148–149. The beneficial activity of the agent of the invention in this use is determined e.g. as follows:

1. MIC values:

Nine field isolates of WBHS from outbreaks of swine dysentery are included from herds with and without diarrhoea, and ATCC 29796 (*Serpulina innocens*, group 3) (Fellström, C., *Res. Vet. Sci.* 59 [1995] 1–4. Identification is based on pattern of hemolysis on TSA (Tryticase soy agar) with 5% bovine blood, and on test for indole production and hippurate hydrolysis (Rosco Diagnostic Tablets, Taastrup, DK). Of the nine weakly beta-hemolytic spirochetes, one was assigned to group 2, four to group 3, and five to group 4 (Fellström, ibid.). The bacteria are transferred from agar plates into 0.9% saline and turbidity adjusted to 1.0 on the McFarland scale before 10 µl of each isolate is inoculated on agar plates with two-fold concentrations of the following antimicrobials: valnemulin hydrochloride, tiamulin hydrogen fumarate, dimetridazole, lincomycin hydrochloride, and tylosin. Growth and hemolysis are recorded after 4 days of growth anaerobically and MIC is determined as the lowest concentration of antibiotics where the spirochetes do not grow.

The results of the MIC determinations for WBHS are shown in Table 6. Generally, the WBHS were susceptible to all of the five antimicrobials. There were no differences in susceptibility between the three groups of WBHS for any of the antimicrobials under test. The MIC values obtained for valnemulin are at the lowest value for 9 out of 10 strains, while they are much higher for the vast majority of the strains with all 4 reference compounds.

The high susceptibility of valnemulin for both WBHS makes it interesting for use in the treatment of clinical cases in infected herds.

TABLE 6

Minimal inhibitory concentration (MIC) values for 10 weakly beta-hemolytic spirochetes

| MIC (μg/ml) | Antimicrobial[1] | | | | |
|---|---|---|---|---|---|
| | Valnemulin (ch) | Tiamulin (hfu) | Dimetri-dazole | Lincomycin | Tylosin |
| 0.0156 | 9 | 4 | | | |
| 0.0312 | — | 2 | | | |
| 0.0625 | — | 3 | 2 | | |
| 0.125 | | — | 4 | | |
| 0.250 | | — | 4 | | |
| 0.500 | | — | — | 4 | |
| 1 | 1 | 1 | — | 1 | |
| 2 | | | — | | 2 |
| 4 | | | | | |
| 8 | | | | — | 1 |
| 16 | | | | — | |
| 32 | | | | 1 | |
| 64 | | | | 1 | |
| 128 | | | | 3 | — |
| >128 | | | | — | 7 |

[1] The figure is the number of weakly beta-hemolytic spirochetes determined as having that MIC value
ch = hydrochloride; hfu = hydrogen fumarate The agent of the invention is therefore useful in the therapy of swine colitis associated with *Serpulina pilosicoli* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at a daily dosage of from about 1 mg/kg to about 5 mg/kg animal body weight, suitably given in divided doses two to four times daily or ad libitum in feed or water, or in sustained release form. For most animals the total daily dosage is from about 10 mg to about 400 mg, e.g. from about 10 mg to about 200 mg for prevention or about 20 mg to about 400 mg for treatment, given ad libitum in feed or water, or once or twice daily.

Preferred doses in drinking water are from 0.001 to 0.05% weight by volume, particularly 0.001 to 0.005%, and in feed from 20 to 100 g/metric tonne, particularly 20 to 75 g/metric tonne.

D) Ileitis in swine associated with *Lawsonia intracellularis* infection:

*Lawsonia intracellularis* infection may be diagnosed in conventional manner, e.g. as described in veterinary manuals such as Taylor, D. J., in *Pig Diseases*, 6th Ed. (1995), Publ. D. J. Taylor, Glasgow, U.K. on pages 154–157. The beneficial activity of the agent of the invention in this use is determined e.g. as follows:
1. Activity in vitro:

The method of Lawson, G. H. K. et al., *J. Clin. Microbiol.* 31 (1993) 1136–1142 is generally followed, with some modifications (standard Kirby-Bauer disc methods are not applicable to intracellular bacteria):

Cells: Monolayers of IEC-18 rat enterocyte cell cultures (ATCC CRL 1589) are established and maintained by standard cell culture methods. One day old monolayers of dividing cells (approx. 30% confluence) are prepared for infection on day 0, on glass coverslips in small culture vials (Tracs).

Inocula: Batches of three strains of *Lawsonia intracellularis* are used as inocula. These are derived from pigs afflicted with proliferative enteropathy, of the proliferative haemorrhagic enteropathy (PHE) and porcine intestinal adenomatosis (PIA) forms prepared from pig intestines, and passaged in cell cultures as described in the above Lawson reference. The two PHE strains were partly tested for pathogenicity in pigs as described in McOrist, S. et al., *Infect. Immun.* 61 (1993) 4286–4292. Inocula batches are collected after several cell passages, and stored frozen at −70° C. in 1 ml vials. Preliminary trials established appropriate dilutions of thawed vials that would result in readily recognizeable cell infections in 5 day trials.

Antibiotics are prepared as 100× stock solutions for each use. Activity of each batch of antibiotic is confirmed by standard Kirby-Bauer disc methods with a laboratory strain of *Escherichia coli*.

Infections: On day 0, a vial of each strain is thawed, diluted 1/8 to 1/32 with culture medium, for use in four groups 1 to 4.

For group 4 (continuous treatment) this inoculum is initially incubated for one hour at 37° C. in culture medium containing the antibiotic at various concentrations prior to addition to cells.

For group 3 (extracellular activity) this inoculum is prepared in culture medium, containing the antibiotic at various concentrations added immediately prior to time of addition to cells.

For groups 1 (control) and 2 (intracellular activity) inocula are prepared in culture medium free of antibiotics and added to cells. Culture vials (Tracs) with cells with added inocula (+/− antibiotics) in a total of 0.5 ml of medium are placed in steel jars, evacuated to 40% atmosphere (8% $O_2$), left for 2 min, replenished with hydrogen and finally 10% $CO_2$. Tracs are then removed from these jars and placed into an incubator set to provide a humidified atmosphere of 8% $O_2$, 8.8% $CO_2$ and the remainder nitrogen, at 37° C.

On days 1 and 2 all vials are removed and refed with fresh medium, either containing antibiotics, groups 2 and 4, or not, groups 1 and 3, and replaced into the incubator. On day 5, all coverslips are removed and stained for *Lawsonia intracellularis* by indirect immunoperoxidase stain incorporating a specific monoclonal antibody. The number of cells on each coverslip, heavily infected with *Lawsonia intracellularis* (>30 per cell, heavily infected cell=HIC) is used as the main measure of infection. The number of foci of HIC and general cell observations are also noted. HIC in control (group 1), intracellularly active antibiotic assay (group 2), extracelluiarly active antibiotic assay (group 3) and continuous treatment assay (group 4) are compared in triplicate assays, for up to 3 strains each. Some assay are repeated for various inocula strengths. Percentage ratios are calculated after derivation of the mean HIC of the controls relevant to the test group. Mean control HIC is the total number of HIC in control Tracs divided by the number of infected control Tracs. The percentage ratio of test Tracs is then calculated by dividing their HIC value by the mean control HIC, multiplied by 100 to give a percentage. That is, test Tracs where antibiotics has no effect would have a percentage ratio of around 100 and where antibiotics completely inhibits growth, the ratio would 0.

The results obtained with valnemulin hydrochloride are as appears from Table 7 which shows the percentage of cells remaining uninfected after treatment:

TABLE 7

Percentage ratios of Lawsonia intracellularis infection of cell cultures with added valnemulin

| Valnemulin (ch) concentration | Strain group | | | Strain group | | |
|---|---|---|---|---|---|---|
| (µg/ml) | 2 | 3 | 4 | 2 | 3 | 4 |
| 8 | 0 | 0 | 0 | 0.86 | 0.2 | 0.5 |
|   | 0 | 0 | 0 | 0 | 0 | 1.4 |
|   | 0 | 0 | 0 | 0 | 1.4 | 0.2 |
| 4 |   |   |   | 0 | 0 | 0.8 |
|   |   |   |   | 0 | 0.83 | 2.5 |
|   |   |   |   | 1.7 | 1.7 | 2.5 |
| 2 | 0 | 0 | 0 |   |   |   |
|   | 0 | 0 | 0 |   |   |   |
|   | 0 | — | 28 |   |   |   | ch = hydrochloride

These results indicate that the minimum concentration of valnemulin hydrochloride to cause significant inhibition of the growth of Lawsonia intracellularis (<1% growth) is <2 µg/ml.

2. Challenge study:

Thirty-five weaner pigs are challenged on the same day with a virulent inoculum of Lawsonia intracellularis (strain LR189/5/83), an isolate of the causative agent of porcine proliferative enteropathy obtained by culture in the rat enterocyte cell line IEC-18 (ATCC CRL 1589) as described in Lawson et al., J. Clin. Microbiol. 31 (1993) 1136–1142. Seven control pigs are dosed with a buffer solution. Seven of the 21 challenge pigs are left untreated. These seven pigs had reduced weight gains and all developed lesions of proliferative enteropathy, detected in sections of the intestines taken at necropsy three weeks after challenge. Six of these 7 pigs had grossly visible lesions, three had mild to moderate diarrhea two weeks after challenge. To test a "prevention" dosing strategy, two other groups of challenged pigs are dosed orally with valnemulin hydrochloride at the doses of 25 ppm and 75 ppm, respectively (i.e. 1.25 mglkg and 3.7 mg/kg) via a premix given two days before challenge, continuing until euthanasia. To test a "treatment" strategy two other groups of challenged pigs are dosed orally with valnemulin 25 ppm and 75 ppm via a premix given seven days after challenge, continuing until euthanasia.

No lesions of proliferative enteropathy in sections of the intestines taken at the necropsy were visible in 3 of 7 pigs in the prevention group and in 5 of 7 pigs in the treatment group. Control pigs remained normal. Therefore valnemulin prevented or treated the disease in a large proportion of challenged pigs even at the low actual doses of medication received.

The agent of the invention is therefore useful in the therapy of ileitis in swine associated with Lawsonia intracellularis infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at a daily dosage of from about 1.5 mg/kg to about 6.5 mg/kg animal body weight, suitably given ad libitum in water or feed, or in divided doses two to four times daily, or in sustained release form. For most animals the total daily dosage is from about 10 mg to about 1000 mg, preferably from about 15 mg to about 500 mg, given once or twice daily.

Preferred doses in drinking water are from 0.001 to 0.05% weight by volume, particularly 0.001 to 0.005%, and in feed from 20 to 400 g/metric tonne, particularly 20 to 200 g/metric tonne.

E) Chronic respiratory disease and arthritis in poultry associated with Mycoplasma gallisepticum infection:

Infection may be diagnosed in conventional manner, e.g., for Mycoplasma gallisepticum infection, as described in veterinary manuals such as Diseases of Poultry, 8th Ed. (1984), Ed. Hofstad et al., Iowa State University Press, on pages 196–198. The beneficial activity of the agent of the invention in this use is determined e.g. as follows:

1. Activity in vitro: MIC

The antimicrobial effect of vainemulin hydrochloride is determined by means of a standard serial microdilution technique in comparison to tylosin (Tylan soluble) and tiamulin hydrogen fumarate.

12.8 mg of the test compound are dissolved in 100 ml of distilled water to obtain a stock solution which is stored at $-20°$ C. until used. Mycoplasma gallisepticum reference strain used are X95, S6 Holland, S6 Bench (England), MS-16 (Japan), MK-7 (Japan) and 1226, and various fresh field isolates.

The antibiotic-sensitivity of the strains is examined using a modified microbroth dilution procedure (Stipkovits et al., Vet. Microbiol. 15 [1987] 65–70). Testing medium is added (100 µl) to all the wells of microtitration plates, using doubling dilutions of antibiotics. The inoculum (100 µl) contains $10^5$ cfu/ml. The plates are sealed with sellotape and incubated at 37° C. over a period of 3 days. The lowest concentration of the antibiotic completely preventing colour change of the media at the third day reading is the minimal inhibitory concentration (MIC). The wells without colour range are checked for viability of mycoplasmas by plating them on agar medium. All Mycoplasma strains are propagated in 10 ml of medium B (Ernø, H. and Stipkovits, L., Acta Vet. Scand. 14 [1973] 436–449). After incubation at 37° C. until early log phase of growth, 1 ml aliquots of culture are dispensed in tubes as seed cultures and stored at −20° C. The glucose fermenting Mycoplasma strains are tested in modified medium Bg supplemented with 1% glucose (pH 7.8), the arginine hydrolysing strains in medium Ba (Ernø, H. and Stipkovits, L., supra, 450–463) containing 1% arginine (pH 7.3) and the glucose- and arginine-negative strains in medium B including 1% triphenyltetrazolium chloride.

The average MIC values for different strain groups and antibiotics taking into consideration dilutions are calculated.

The MIC values of reference strains are shown in Table 8, those of Mycoplasma isolates in Table 9:

TABLE 8

MIC values of Mycoplasma gallisepticum reference strains (µg/ml)

| Strains | Valnemulin (ch) | Tiamulin (hfu) | Tylosin |
|---|---|---|---|
| Bench | 0.0312 | 0.0312 | 0.0312 |
| Holland | 0.0312 | 0.0312 | 0.0312 |
| MK-7 | 0.0078 | 0.0312 | 0.0312 |
| MS-16 | 0.0312 | 0.0312 | 0.0312 |
| 1226 | 0.0312 | 0.25 | 0.0312 | ch = hydrochloride  hfu = hydrogen fumarate

TABLE 9

MIC values of mycoplasma isolates of chicken origin (μg/ml)

| Isolate | Valnemulin (ch) | Tiamulin (hfu) | Tylosin |
|---|---|---|---|
| 20002 | 0.0625 | 0.25 | 0.25 |
| 20006 | 0.0625 | 0.0625 | 0.25 |
| 20008 | 0.0625 | 0.0625 | 0.0625 |
| 20174 | 0.0625 | 0.25 | 0.25 |
| 20175 | 0.0625 | 0.5 | 2.0 |
| 20176 | 0.0625 | 0.25 | 2.0 |
| 20177 | 0.0625 | 0.25 | 1.0 |
| 20178 | 0.0625 | 0.5 | 2.0 |
| 20224 | 0.0312 | 1.0 | 4.0 |
| 20312 | 0.0312 | 0.25 | 4.0 |
| 20321 | 0.0312 | 0.0312 | 0.5 |
| 20472 | 0.0312 | 1.0 | 16.0 |
| 20473 | 0.0312 | 0.5 | 32.0 |
| 20474 | 0.0312 | 1.0 | 16.0 |
| 20475 | 0.0312 | 0.5 | 32.0 |

Results obtained with reference mycoplasma strains indicate that the three compounds show more or less the same activity range. MIC values of avian field isolates, however, reflect a pronounced difference between the test substances: whereas a uniformly high sensitivity against valnemulin (0.03–0.06 μg/ml) is displayed, the sensitivity against tiamulin is somewhat reduced (0.06–1 μg/ml), and with tylosin even resistant strains are obvious (0.06–32 μg/ml).

2. Challencge studies:

2.1. Prevention

Groups of male broiler chickens are infected with a virulent strain of *Mycoplasma gallisepticum* (MG) and each group medicated respectively with one of the following: valnemulin (concentrations of 0.00312, 0.00625, 0.0125 and 0.025%), tiamulin (0.00625, 0.0125 and 0.025%), and tylosin (0.05%). Infection is effected on day 2 by injection of 0.1 ml of *Mycoplasma gallisepticum* culture containing approximately 106 cfu of viable organisms into each lung (Jordan, F. T. W., *The Veterinary Record* 127 [1990] 502) and medication is commenced within an hour of infection and continued for three consecutive days. There is also an infected untreated group and an uninfected group.

The results obtained show that prevention of clinical signs and mortality were equally satisfactory for groups medicated with the two higher doses of valnemulin (0.0125 and 0.025%), the three doses of tiamulin, and the concentration of tylosin. Lesions were seen in fewer chicks and were less severe with tylosin, followed by tiamulin and then the two higher doses of valnemulin (0.0125 and 0.025%). The 2 lower doses of valnemulin were less effective in this respect. The greatest weight gains were for the groups medicated with tylosin; next but significantly less (p<0.05) were the group of uninfected birds, those on tiamulin and those given valnemulin on all but the lowest dose. The lowest weight gains were obtained with the groups medicated with the lowest dose of valnemulin and the infected unmedicated group and they were not significantly different. MG was not recovered during life or at necropsy from the uninfected group, the chicks on the highest dose of tiamulin and on tylosin and was isolated from only one bird from the group on the highest dose of valnemulin. A higher proportion of isolations were made from all other infected groups. The serological results did not entirely reflect this for tylosin since there was a relatively high proportion of positive reactors in this group.

Thus the two higher doses of valnemulin were found to be as effective as the reference compounds in preventing *Mycoplasma gallisepticum* infection in the young chick.

2.2. Treatment:

Groups of male broiler chicks are infected with a virulent strain of *Mycoplasma gallisepticum* (MG) and each group medicated respectively with valnemulin at a concentration of 0.0125%, 0.025%, 0.05%, tiamulin at the same concentration, tylosin 0.05% and a lincospectin, spectinomycin combination (Linco-Spectin) 0.083%. There is also one infected group left untreated and an uninfected group. The chicks are infected at two days of age by the injection of $3.4 \times 10^5$ organisms into each lung. Medication in the drinking water is commenced 24 hours later for three successive days except for Linco-Spectin with which treatment was continued for 5 days.

Results obtained show that control of mortality, with no more than 5%, was best with all three concentrations of vainemulin, and with tiamulin at 0.05%. Lesions were not seen in chicks medicated with the highest and lowest doses of valnemulin and in only a few receiving tiamulin and tylosin. Weight gains for valnemulin at all concentrations were higher than for the tiamulin treated groups and equal to the tylosin group. Mycoplasma were not recovered, at the termination of the experiment at 23 days, from the 3 groups of birds on valnemulin and those given tylosin. In the serological results, at this time, there were some positive reactors in all infected groups.

In consideration of mortality, weight gain, isolation of MG and the results of serum agglutination tests, the two higher doses (at 0.025% and 0.05%) of valnemulin given in the drinking water give results at least as good as or better than tiamulin at 0.05% or tylosin at 0.05% and very much better than Linco-Spectin.

The agent of the invention is therefore useful in the therapy of chronic respiratory disease and arthritis in poultry associated with *Mycoplasma gallisepticum* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered in drinking water at dosages of from about 0.005 to about 0.05% weight by volume, particularly 0.01 to 0.03%, and in feed from 20 to 400 g/metric tonne, particularly 20 to 200 g/metric tonne.

F) Secondary infection with *Pasteurella multocida, Actinobacillus* (Haemophilus) *pleuropneumoniae* and/or *Haemophilus parasuis* infection:

Secondary infection with *Pasteurella multocida, Actinobacillus* (Haemophilus) *pleuropneumoniae* and/or *Haemophilus parasuis* may be diagnosed in conventional manner, e.g. as described in veterinary manuals such as Taylor, D. J., in *Pigs Diseases*, 6th Ed., (1995), Publ. D. J. Taylor, Glasgow, U.K., on pages 185–187; 188–194; and 194–197. The beneficial activity of the agent of the invention in this use is determined e.g. als follows:

The minimal inhibitory concentration (MIC) of valnemulin hydrochloride against recent isolates of *Pasteurelia multocida, Haemophilus pleuropneumoniae* and *Haemophilus parasuis* originating from porcine respiratory material is determined and compared with tiamulin. Cultures of bacterial isolates comprising 10 *P. multocida*, 10 *H. pleuropneumoniae* and 3 *H. parasuis* are used, isolated within the last 5 years from diseased pigs as assessed at post-mortem examinations. Three of the Pasteurella isolates were toxigenic strains of *Pasteurella multocida*. For *H. pleuropneumoniae* and *H. parasuis*, on the day before testing a single loopful of each of the pure cultures is inoculated into 10 ml of Todd & Hewitt broth (Unipath CM190) containing 1% donor calf serum and 2 mg per ml of nicotinamide adenine dinucleotide (NAD). For *P. multocida*, on the day of testing a single loopful of each of the pure cultures is inoculated into 10 ml of nutrient broth No. 2 (Unipath CM67) containing 1% donor calf serum. Each of the prepared broth cultures are incubated for 18 hours at 37° C. in 10% $CO_2$. After incubation and on the day of testing the 23 broth cultures are adjusted down to $10^5$–$10^6$ organisms per ml in sterile physiological saline in preparation for inoculation of the MIC culture medium. For each test compound, standard control cultures of Oxford Staphylococcus aureus NCTC 6571 are also set up to validate the results of the MIC tests. In each case, broth cultures set up from the control organisms are identical to those of the organisms under test. Valnemulin is a hydrochloride, tiamulin is used as the hydrogen fumarate. On the days of testing stock solutions of the test compounds containing 3.2 mg/ml of active ingredient are prepared in sterile distilled water. Nine two-fold dilutions are then further prepared in sterile distilled water giving a range for each antibiotic of 320 μg down to 1.25 μg per ml for incorporation into the MIC medium. Sensitised agar (Oxoid CM409) containing lysed horse blood (Oxoid SR50) is prepared according to the manufacturer's recommendations and adjusted to pH 7.4 it necessary. For all batches of MIC medium prepared for the MIC assays against the two Haemophilus species, 2 mg per ml of NAD is added to provide the necessary growth factor. 18 ml of molten agar (50° C.) is mixed with 2 ml (one in ten dilutions) of each of the prepared dilutions of test compound in 90 mm Petri dishes. Four replicate plates are prepared from each dilution. For each MIC assay, 4 replicate plates containing 18 ml of agar and 2 ml of sterile distilled water are also prepared to act as growth indicators.

The dried MIC plates are inoculated with 0.2 μl of the prepared test organisms, those with *P. multocida* are incubated in air at 37° C. for 18 hours, and those inoculated with *H. pleuropneumoniae* and *H. parasuis* are incubated at 37° C. for 18 hours in 10% $CO_2$. After inoculation the growth of the organisms is examined initially by eye followed by microscopic examination on a stereo zoom microscope. The MIC value is taken as the lowest concentration of test compound at which no growth can be detected at the point of inoculation on all four plates by microscopic examination. The results obtained are as appears from the Table 10:

TABLE 10

MICs (μg/ml)

| Pathogen | Compound | |
|---|---|---|
| | Valnemulin (ch) | Tiamulin (hfu) |
| *Pasteurella multocida* | | |
| Range | 2.0–8.0 | 4.0–16 |
| Mean | 3.8 | 9.2 |
| *Haemophilus pleuropneumoniae* | | |
| Range | 0.125–4.0 | 0.125–16 |
| Mean | 0.85 | 4.5 |
| *Haemophilus parasuis* | | |
| Range | 0.25 | 0.5–1.0 |
| Mean | 0.25 | 0.7 | ch = hydrochloride  hfu = hydrogen fumarate

It appears therefrom that valnemulin as compared with tiamulin had a mean two and a half fold increase in activity against *P. multocida*, a five and a half fold increase against *H. pleuropneumoniae* and a three fold increase against *H. parasuis*.

The agent of the invention is therefore useful in the therapy of secondary pneumonia in swine associated with *Pasteurella multocida, Actinobacillus* (Haemophilus) *pleuropneumoniae* and/or *Haemophilus parasuis* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at a daily dosage of from about 5 mg/kg to about 15 mg/kg animal body weight, suitably given ad libitum in water or feed, or in divided doses two to four times daily, or in sustained release form. For most animals the total daily dosage is from about 100 mg to about 1000 mg, preferably from about 100 mg to about 500 mg, given once or twice daily.

It may advantageously be administered as sole therapy.

Preferred doses in drinking water are from 0.01 to 0.05% weight by volume, particularly 0.01 to 0.025%, and in feed from 100 to 400 ppm (g/metric tonne), particularly 100 to 200 ppm.

G) Pneumonia in lambs, sheeps and cattle associated with *Pasteurella haemolltica* infection:

*Pasteurella haemolytica* infection may be diagnosed in conventional manner, e.g. as described in veterinary manuals such as *Veterinary Medicine,* 8th Ed. (1994), Eds. Radostits, O. M., Blood, D. C. and Gay, C. C., Publ. Bailliere Tindall, London, U.K., on pages 748–770. The beneficial activity of the agent of the invention in this use is determined in vivo e.g. as follows:

The clinical efficacy is determined of two formulations of valnemulin hydrochloride in the treatment of pneumonia in calves due to a controlled infection with *Pasteurella haemolytica* A1:

On day-6, 24 calves that have been nasal swabbed and found to be free of *P. haemolytica* A1 are weighed and allocated to four treatment groups of six, balanced according to live weight with an even distribution of sexes between the groups. The calves are housed in individual pens in a conventional calf rearing unit where they acclimatise for 33 days before allocation. Blood samples are taken twice during the pre-study phase for leukotoxin antibody analysis as a possible indication of prior exposure to *P. haemolytica* A1.

Treatment commences on day-1, approximately 27 hours before the time of challenge:

Group 1—Control;

Group 2—valnemulin hydrochloride 2.5% injectable (2.5 mg/kg twice daily)

Group 3—valnemulin hydrochloride 10% premix orally via calf milk replacer (5.0 mg/kg twice daily);

All calves are challenged on day 0 by endobronchial deposition of 30 ml of *Pasteurella haemolytica* A1 broth culture (M4/l/3, Moredun Research Institute—$1.25 \times 10^7$ cfu/ml) by means of a fibre-optic bronchoscope. Clinical examinations are carried out once daily on days-3 and -2, and twice daily from day-1 to 3. Clinical scores are allocated to each of four parameters: rectal temperature, respiratory rate, nature of respiration and demeanour. Injection sites are also examined. Any calves that are recumbent, and/or showing depression and/or signs of respiratory distress, or which have a total clinical score greater than 5 at a single examination between days 0–3 are euthanased immediately on humane grounds by intravenous administration of a lethal dose of Pentobarbitone Sodium BP(Vet) 20% w/v and necropsied within 24 hours. Calves that survive to day 4 after *P. haemolytica* challenge are euthanased on day 4 following the same procedure as for those euthanased between days 0–3. Lungs are removed from all calves, and assessed visually for consolidated lesions and pleuritic adhesions. Lung tissue samples are excised from eight standard sites and tested for the presence of *P. haemolytica* to determine a value for isolation index. Heart blood swabs are taken from calves that die acutely and tested for the presence of *P. haemolytica*.

Individual calf and group totals, group means and group medians are calculated for all parameters: total clinical score, consolidated lesion score, isolation index, pleuresy score and total score. Individual calf and group totals, group means and group medians are calculated for all categories making up total clinical score: rectal tempereature, respiratory rate, nature of respiration and demeanour. Basic analysis by the Kruskal-Wallis test is applied (Minitab 9) to determine if there is a difference between any of the group scores for each of the parameters: total clinical score, consolidated lesion score, isolation index, pleuresy score and total score. Significance of the Kruskal-Wallis test indicates that the groups are not all the same, not that they are all different. To test which groups are different, pairs of groups are tested using the Mann-Whitney test (Minitab 9).

Compared to untreated calves (Group 1), total clinical scores (p=0.013) were found to be significantly lower in calves that had been treated with valnemulin 10% premix at 5.0 mg/kg/dose twice daily orally via calf milk replacer for five days beginning 27 hours before challenge with *P. haemolytica* A1.

Total clinical scores were also reduced, but not statistically significantly, in calves treated intramuscularly with valnemulin 2.5% injectable at 2.5 mg/kg/dose twice daily for five days beginning 27 hours before challenge with *P. haemolytica* A1.

There were no significant differences between groups that received treatment when total clinical scores were compared.

The agent of the invention is therefore useful in the therapy of pneumonia in lambs, sheep and cattle associated with *Pasteurella haemolytica* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at daily dosages of from about 5 mg/kg to about 15 mg/kg animal body weight, suitably given ad libitum in feed, or in divided doses two to four times daily, or in sustained release form. For most animals the total daily dosage is from about 250 mg to about 3000 mg, preferably from about 250 mg to about 1000 mg, given once or twice daily, or administered ad libitum in feed.

H) Polyarthritis in swine associated with *Mycoplasma hyosynoviae* infection:

*Mycoplasma hyosynoviae* infection may be diagnosed in conventional manner, e.g. as described in veterinary manuals such as Taylor, D. J., in *Pig Diseases,* 6th Ed. (1995), Publ. D. J. Taylor, Glasgow, U.K., pages 172–173. The beneficial activity of the agent of the invention in this use is determined e.g. as follows:

1. Activity in tissue isolates in vitro (MIC assay):

Tissue samples are obtained from the lungs of pigs from various enzootic pneumonia of pigs (EPP)—affected herds. Samples are shipped on dry ice for culture. Four isolates from lung samples initially isolated for recovery of *Mycoplasma hyopneumoniae* were reisolated for *Mycoplasma hyosynoviae* after it had been noted from the lung samples submitted (re-stored at −70° C.), during culture for *M. hyopneumoniae,* that some samples yielded luxuriant growth of colonies having the typical morphology of *Mycoplasma hyosynoviae*. Three further isolates were recovered from other lung samples provided. All isolates were serologically identified by disc growth inhibition with specific rabbit antiserum raised against *Mycoplasma hyosynoviae*. A commerically available solid medium (Mycoplasma Experience Ltd.) is used to isolate *M. hyosynoviae* from lung tissue. A liquid medium (Mycoplasma Experience Ltd.) containing phenol red and arginine (pH 7.0) is used for the MIC assay.

Stock solutions of test compound are prepared at 1 mg/ml concentration in deionised water, sterilised by filtration through $0.2\mu$ pore size membrane filters (Sartorius Minisart, N) and stored at −20° C. For use in the MIC tests the stock solutions are diluted in liquid medium to double the final concentrations required. MIC tests are carried out according to the method of Tanner and Wu, *Avian Diseases* 36 (1992) 714–717. Actively growing challenge cultures are prepared either from 1 ml aliquots of broth cultures stored at −70° C. or from cultures stored on agar at −70° C. The challenge cultures are diluted to give a target titre of $10^3$ to $10^5$ colour changing units/ml. 0.1 ml aliquots of challenge inocula are mixed with 0.1 ml aliquots of antibiotic dilution in microtitre wells. Each microtitre plate contains uninoculated media at pH 7.6 (end point control) and antibiotic-free inoculated challenge controls. All plates are sealed with adhesive film and incubated aerobically at 36° C. MICs are recorded when the colour change in the challenge control wells matches the pH of the end point control. The MIC is the lowest concentration showing no colour change.

The results obtained are shown in Table 11 for valnemulin hydrochloride and two reference compounds, tiamulin hydrogen fumarate and enrofloxacin:

TABLE 11

In vitro sensitivity of 7 field isolates of *Mycoplasma hyosynoviae*

| Compound | MIC range ($\mu$g/ml) |
|---|---|
| Valnemulin hydrochloride | 0.0001–0.0005 |
| Tiamulin hydrogen fumarate | 0.0025–0.025 |
| Enrofloxacin | 0.025–0.25 |

The sensitivities of the seven field isolates of *Mycoplasma hyosynoviae* to vatnemulin are much higher than for the other two compounds, indicating that recent field isolates are extremely sensitive to valnemulin.

The agent of the invention is therefore useful in the therapy of polyarthritis in swine associated with *Mycoplasma hyosynoviae* infection. For this use, the effective dosage will, of course, vary depending on the particular salt employed, the mode of administration, the size and age of the animal and the effect desired; for example for prophylactic treatment relatively low doses would be administered over a long time. However, in general, satisfactory results are obtained when the agent is administered at a daily dosage of from about 5 mg/kg to about 15 mg/kg animal body weight, suitably given ad libitum in water or feed, or in divided doses two to four times daily, or in sustained release form. For most animals the total daily dosage is from about 100 mg to about 1000 mg, preferably from about 100 mg to about 500 mg, given once or twice daily.

It may advantageously be administered as sole therapy.

Preferred doses in drinking water are from 0.01 to 0.05% weight by volume, particularly 0.01 to 0.02 5%, an d in feed from 100 to 400 ppm (g/metric tonne), particularly 100 to 200 ppm (g/metric tonne).

For all these uses the compound may be used in tree base form or in veterinarily acceptable salt form, e.g. quaternary salt or, especially, acid addition salt form. Such salt forms exhibit the same order of activity as the free base form. Examples of suitable acid addition salts are the hydrogen fumarate, fumarate, naphthalin-1,5-sulphonate and especially the hydrochloride.

The agent of the invention may be administered orally, locally or parenterally and admixed with conventional chemotherapeutically acceptable diluents and carriers and, optionally, other excipients and administered in such forms as tablets, capsules or injectable preparations. It also forms an excellent additive for feed mixes (as premix) or for drinking water.

Preferred veterinarily acceptable carriers include e.g. commonly used pharmaceutical excipients like sugar, corn starch, lactose, cellulose, as well as grain carrier systems and grain by-products like ground rice hulls, wheat middlings and soy flour; furthermore, solid diluents like ground limestone, sodium sulfate, calcium carbonate and kaolin, or liquid substances like veterinarily acceptable oils (vegetable oils or mineral oil), propyleneglycol and polytheleneglycol. Suitably these formulations are administered to the animal orally, preferably mixed into feed in form of medicated meal feed or medicated pellets.

For applications in drinking water, solutions in water with or without solvents such as ethanol, propyleneglycol, polyethyleneglycol, approved liquid surfactants and sorbitol are used.

For e.g. intramuscular injection the formulation is typically prepared as a solution in water which may contain solvents like ethanol or propyleneglycol, or in a veterinarily acceptable oil. Examples of acceptable oils are sesame oil, medium chain triglycerides (e.g. Miglyol), isopropyl myristate and ethyl oleate. The formulation may contain preservatives, buffers and other common excipients.

Veterinary formulations for use in the present invention may be prepared by mixing the ingredients in the required proportions. The formulation is then packaged into an appropriate container ready for administration.

The following Example illustrates the invention:

| Ingredient | Amount (g/100 ml) |
|---|---|
| valnemulin hydrochloride | 10.0 |
| phenol | 0.5 |
| Miglyol 840 | to 100 ml |

The agent of the invention is well tolerated. The acute toxicity in the rat of the compound of formula I in hydrochloride salt form was determined with single doses of 1000 mg/kg and 2000 mg/kg orally administered to 5 male and 5 female rats per dose group. Deaths occurred within 1–8 days. The $LD_{50}$-value obtained is >1000 mg/kg p.o.

What is claimed is:

1. A method of treating veterinary disease in animals involving secondary infections due to increased stocking density, wherein the veterinary disease is associated with infection by bacteria selected from the group consisting of *Serpulina pilosicoli, Lawsonia intracellularis, Pasteurella multocida, Pasteurella haemolytica,* and mixtures thereof, wherein the method comprises administering to the animal a therapeutically effective amount of the compound of formula I

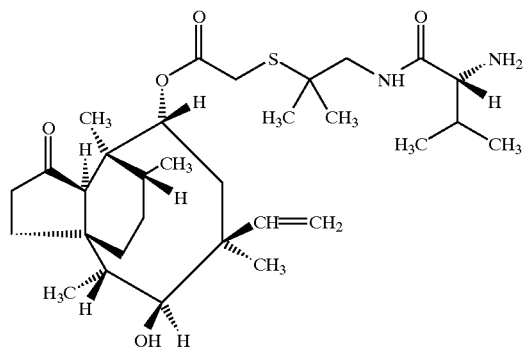

in free base or in a veterinarily acceptable form.

2. The method of claim 1, wherein the compound of formula I is administered to swine in need of such treatment.

3. The method of claim 1, wherein the compound of formula I is administered together with at least one veterinarily acceptable carrier or diluent.

4. The method of claim 1, wherein the compound of formula I is administered in free base or in veterinarily acceptable salt form to swine for the treatment of swine colitis associated with *Serpulina pilosicoli* infection.

5. The method of claim 1, wherein the compound of formula I is administered in free base or in veterinarily acceptable salt form to swine for the treatment of ileitis associated with *Lawsonia intracellularis* infection.

6. The method of claim 1, wherein the compound of formula I is administered in free base or in veterinarily acceptable salt form for the treatment of veterinary disease associated with *Pasteurella multocida* infection.

7. The method of claim 1, wherein the compound of formula I is administered in free base or in veterinarily acceptable salt form to lamb, sheep, or cattle for the treatment of pneumonia associated with *Pasteurella haemolytica* infection.

8. The meted of claim 1, wherein the compound of formula I is administered in hydrochloride acid addition salt form.

9. A process for the preparation of a medicament for the treatment of veterinary disease in animals involving secondary infections due to increased stocking density wherein the veterinary disease is associated with infection by bacteria selected from the group consisting of *Serpulina pilosicoli, Lawsonia intracellularis, Pasteurella multocida, Pasteurella haemolytica,* and mixtures thereof, wherein the method comprises combining a therapeutically effective amount of the compound of formula I (I)

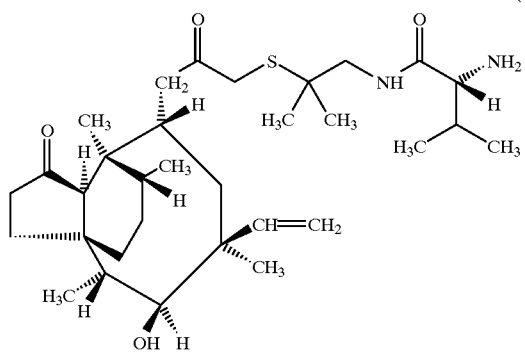

in free base or in a veterinarily acceptable form together with at least one veterinarily acceptable carrier or diluent.

10. A method of treating veterinary disease in animals wherein the veterinary disease is selected from the group consisting of swine colitis and ileitis in swine comprising administering to the animal a therapeutically effective amount of the compound of formula I (I)

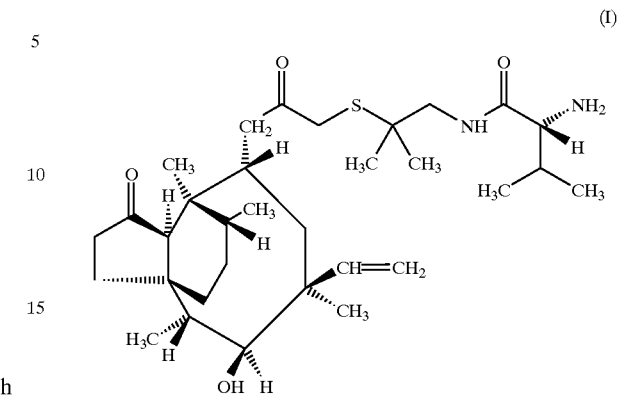

in free base or in veterinarily acceptable form.

* * * * *